United States Patent [19]
Mannix

[11] Patent Number: 5,385,559
[45] Date of Patent: Jan. 31, 1995

[54] SYRINGE FILLING AND METERING DEVICE

[75] Inventor: Gerald Mannix, Miramar, Fla.

[73] Assignee: R. Jason Newsom, Miami, Fla.

[21] Appl. No.: 169,045

[22] Filed: Dec. 20, 1993

[51] Int. Cl.$^6$ .......................... A61M 5/00; B65B 1/04
[52] U.S. Cl. ...................................... 604/211; 141/27; 604/207
[58] Field of Search ................ 604/82, 83, 86–88, 604/207–211; 141/27, 95, 330, 375, 383, 384

[56] References Cited

U.S. PATENT DOCUMENTS

| | | | |
|---|---|---|---|
| 2,861,570 | 11/1958 | Beecher | 141/27 X |
| 3,844,318 | 10/1974 | Raia et al. | 141/27 |
| 3,875,979 | 4/1975 | Hults | 141/27 |
| 4,217,055 | 8/1980 | Wright | 141/27 |
| 4,252,159 | 2/1981 | Maki | 141/27 |
| 4,357,971 | 11/1982 | Friedman | 141/27 |
| 4,466,426 | 8/1984 | Blackman | 604/210 X |
| 4,883,101 | 11/1989 | Strong | 141/27 |
| 5,247,972 | 9/1993 | Tetreault | 141/27 |
| 5,292,318 | 3/1994 | Haber et al. | 604/407 |

FOREIGN PATENT DOCUMENTS

| | | | |
|---|---|---|---|
| 362004 | 10/1922 | Germany | 141/383 |
| 669996 | 1/1939 | Germany | 141/383 |

Primary Examiner—John D. Yasko
Assistant Examiner—Adam J. Cermak
Attorney, Agent, or Firm—Malloy & Malloy

[57] ABSTRACT

A filling and metering assembly designed to fill syringes accurately by a sightless person wherein the assembly includes an elongated base having an open side exposing an interior surface which is specifically configured to removably position and hold a syringe and a medicine container therein. Another structure associated with the subject assembly includes an indicator structure associated therewith which is adapted to produce an audible sound capable of being heard by the sightless user of the assembly in the determination of an accurate and desired amount of medicine being passed from the medicine container to the interior of the syringe.

5 Claims, 1 Drawing Sheet

U.S. Patent    Jan. 31, 1995    5,385,559
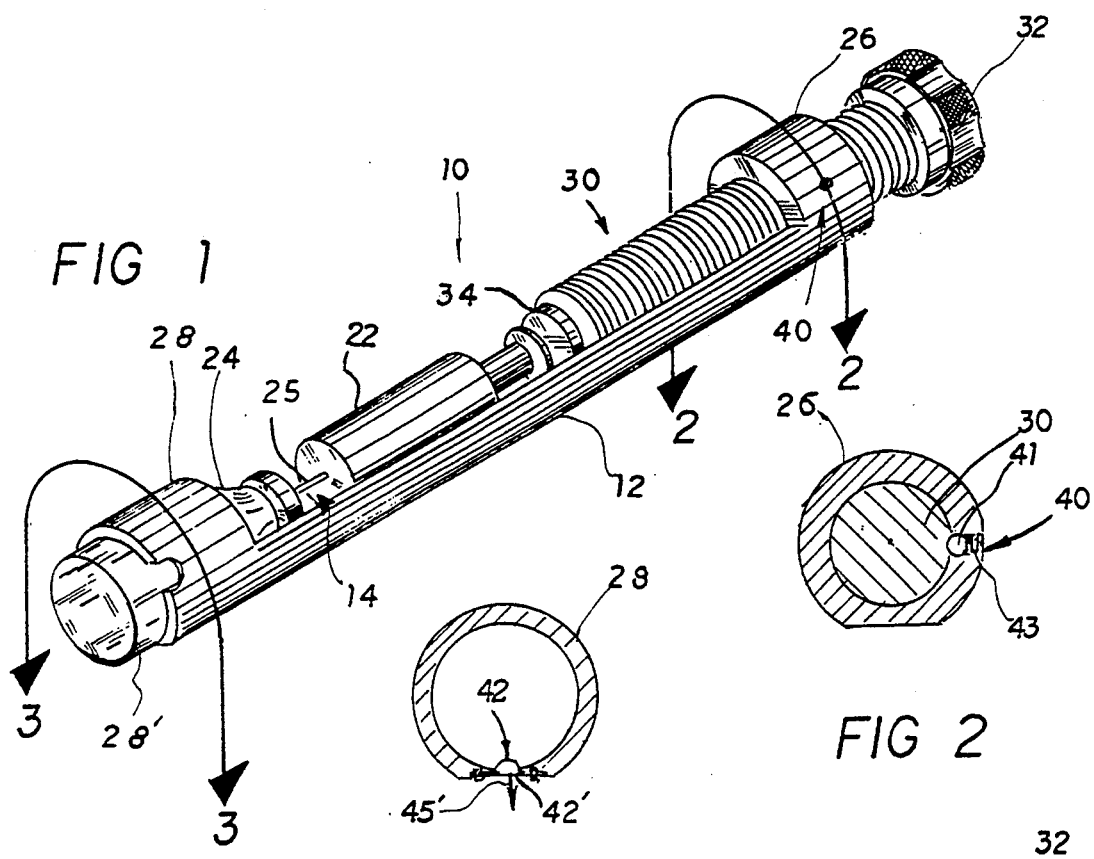
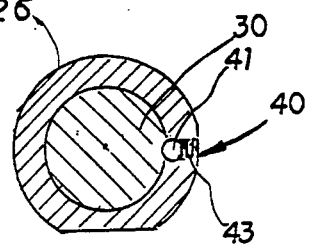
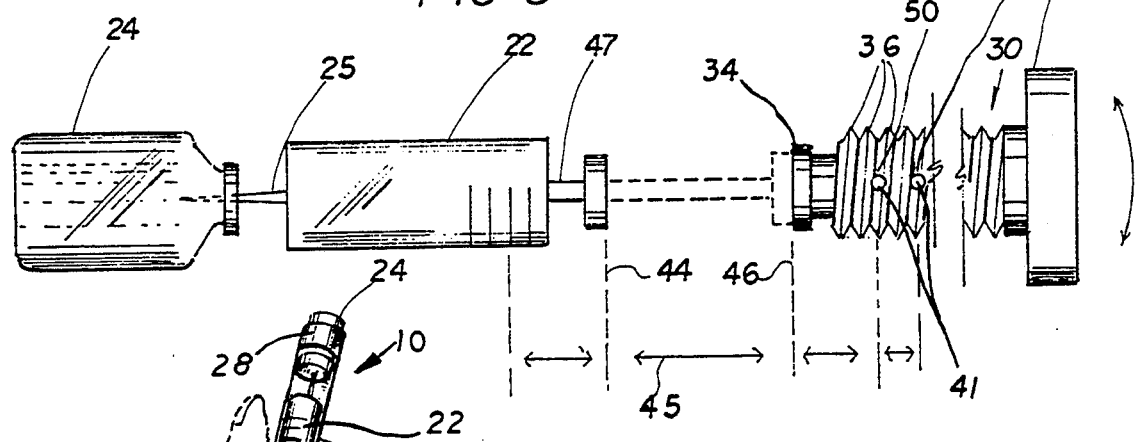
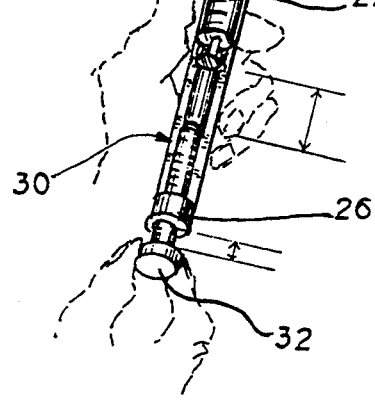
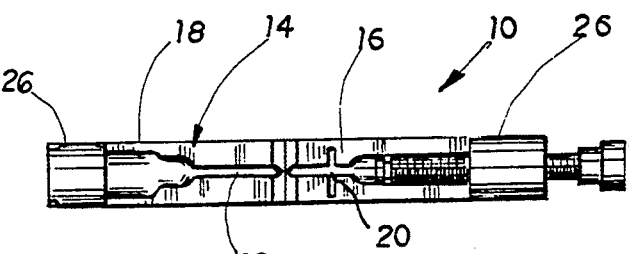

SYRINGE FILLING AND METERING DEVICE

BACKGROUND OF THE INVENTION

1. Field of the Invention

This invention relates to a filling assembly for a syringe which is specifically adapted to be used by sightless people to the extent that an indicator assembly is associated therewith which produces an audible sound to indicate the desired and accurate amount of medicine or liquid being passed from a liquid or medicine container into a syringe mounted on the subject assembly.

2. Description of the Prior Art

In situations where people have certain medical problems requiring that they give themselves accurate doses of medicine there was a continuing problem to accurately transfer the amount of medicine from a conventional medicine container into the syringe. It is important of course that the amount of medicine being injected is accurate. This task is difficult enough for patients with no sight impediments. However, when a patient is sightless or has some type of visual or sight impediment the task becomes even more difficult or even impossible. The present invention is directed to a metering and filling assembly assigned to provide the proper amount of liquid medication from a medicine container into a conventional hypodermic syringe. The structure of such a preferred assembly enables anyone, whether sight impaired or not, to obtain the proper dosage of medication when transferring such medication from a container to a syringe.

Attempts have been made in the prior art to overcome this problem and provide some type of accurate structure which allows a sightless or sight impaired person to accurately transfer the amount of medication to a syringe. However, a vast majority of such attempts, as evidenced by the structure disclosed in the following U.S. Patents are generally overly complicated to the extent that a sightless person has difficulty in operating and/or setting up such structures to accomplish the desired result.

The patent to Maki, U.S. Pat. No. 4,252,159, discloses a dosage device including an elongated substantially flat body on which a syringe is mounted by means of upstanding substantially Y-shaped brackets disposed in spaced apart relation to one another and extending upwardly from a flat exposed surface of the body. An adjustable stop member is provided by being threadedly engaged or mating with an upstanding internally threaded block. Audible sounds are produced by means of an irregularly shaped knob upon each full, 360° rotation by virtue of the knob engaging externally located upstanding lands or like objects. The engagement and sound between the aforementioned knob and the lands depends upon a number of factors which may include flexibility of the base itself or sufficient "play" between the threaded engagement as mentioned above such that the outwardly projected portion of the knob may in fact pass over and in engagement with the upstanding lands. Maki does not show any type of specifically calibrated threaded structure which cooperates with an indicator means such that the passage of one thread beyond the indicator means while being in engagement therewith produces a click for each thread passing the indicator means. Further, there is no showing of a calibration such that each thread producing an audible sound results in one unit volume of liquid capable of being dispensed from a medicine container by movement of the plunger of the syringe.

The patent to Blackman, 4,466,426, discloses a syringe with an actinic ray blocking stripe. A structural provision is included which provides an audible sound upon a plunger being withdrawn from the barrel of a syringe for purposes of filling the syringe. There is no teaching in this structure of a separate mounting base or platform on which a medicine container is mounted along with the syringe such that a specific calibration exists between the threaded engagement of components of a metering means and the specific structural adaptation of an indicator means such that one thread passing by the metering means is indicative, through the production of an audible sound, of one unit volume of medicine capable of being dispensed from the medicine container.

The patent to Strong, U.S. Pat. No. 4,883,101, discloses a filling device for filling an injection syringe which incorporates a sound indicator which may be mechanical, electrical or an electronic sound device. The filling device of this invention mounts a gear which is movable one gear tooth at a time to align a linear gear to which the syringe is mounted. A spring loaded ball bearing is biased against a gear wheel and produces a distinctly audible clicking sound when the gear moves a single notch. These clicking sounds can be counted by a user when the attached syringe holder moves and will accurately indicate the amount of liquid medicine drawn into the syringe. This device, while operating on a sound or audible signal bases is complicated to the extent that a number of movable components including a plurality of rotating gears associated with a linear gear are incorporated in order to allegedly fill the syringe in an accurate manner.

Other patents, set forth hereinafter disclose structures which do not operate in a manner utilizing audible sound. To the contrary, such devices present in the prior art rely on feel or touch rather than incorporating a structure which produces a sound type signal. Such patents include Montada, 4,489,766, disclosing a device for filling a syringe with medicine and is specifically adapted to be used by people with a sight impairment. The device has an elongated body with a recess for receiving a syringe. The body has a gauge recess adjacent to a position where the syringe plunger would be located thereby allowing the syringe plunger to be fully extracted. A plurality of retractable spacers of different thicknesses are located in the gauge recess to limit the extraction of the recess plunger and this gauge controls the quantity of medicine drawn into the syringe.

The patent to Wright, U.S. Pat. No. 4,219,055, discloses a syringe filling aid having a body with a bottle holding means at one end and a hilt engaging portion at the other end for engaging the hilt of a syringe when the needle of this syringe is in the bottle. The hilt engaging portion has a notch in which the syringe can be rested and a plunger stop assembly adjustably fixable to the body for limiting movement to a predetermined dose setting. The structure of the Wright patent discloses no sound or audible signal generating means to indicate the proper dosage being transferred.

Another patent which rely on mechanical components for aiding the sightless or those with sight impaired conditions include Wright, U.S. Pat. No. 3,840,011, disclosing an instrument for transferring specific amounts of fluid from a container to a syringe rely on mechanical means to indicate to the operator the proper dosage being transferred.

On a lesser interest of the patents to Phillips, U.S. Pat. No. 4,758,233, disclosing an applicator to inject a medicine or substance into an animal. Tint, U.S. Pat. No. 3,128,765, discloses a hypodermic syringe and dose dispenser which does not include any type of audible signal for indicating proper dosage transfer, but which does include an elongated externally threaded shaft operating as part of the syringe component for forcing a fluid medicine out of the barrel of the syringe.

While the above noted patents are all directed to structures which attempt to overcome problems associated with dispensing proper dosage of medicine and more particularly to the transferring of proper fluid medicine amounts from a container to a syringe structure, none include an efficient and operable device which the sightless or sight impaired can rely on in terms of accuracy and ease of use and particularly wherein an audible signal generating means serves as the proper indicator to measure proper dosage amount.

SUMMARY OF THE INVENTION

The present invention relates to a syringe filling assembly designed to allow the accurate metering of a fluid medicine from a conventional fluid container into the syringe. Particularly, the subject assembly is adapted for use by sightless operators or those who have some type of sight impairment. More particularly, the subject assembly includes an elongated base having an open side portion along a majority of its length. An interior surface is accessible through the open side portion and this surface is specifically adapted to have a plurality of recesses formed therein. These recesses are dimensioned and configured to removably receive a syringe and conventional container of fluid medicine therein. The base further includes two oppositely disposed ends each of which have an open construction. A first of such open ends is defined by a surrounding collar being open so as to allow an elongated shaft to pass therethrough. Inner surfaces of the collar are internally threaded to cooperate with an external threaded surface along the length of the shaft. Rotation of the shaft causes the shaft to move inwardly or outwardly relative to the interior of the elongated base. An inner, free end of the shaft is disposable into somewhat abutting engagement with the end of the plunger of a conventional hypodermic needle. Withdrawal of the plunger portion of the syringe to fill the panel portion thereof is limited by the position of the innermost end of the elongated, threaded shaft.

The aforementioned recesses are such as to allow the needle attached to the syringe to penetrate and pass to the interior of the bottle of fluid medicine in the conventional fashion such that the syringe, once positioned, is ready for filling.

Other features of the subject syringe filling assembly include an indicator means which is specifically adapted to generate an audible signal or "clicking" sound as the elongated, threaded shaft is rotated into or out of the base. More specifically, a spring biased ball or similar ball bearing member is disposed to engage successively each of the threads of the externally threaded surface of the elongated shaft. When so engaged and due to the spring biasing force of the ball, the ball will retract and then "click" into engagement with the next successive thread. Such engagement will cause successive "clicking" sounds. Each said sound is an indication to the sightless operator that the other shaft has been positioned to allow filling of the syringe one volume unit. The spacing between the individual threads on the elongated shaft are so dimensioned and configured such that one thread passing by the sound indicator will allow the withdrawal of the plunger of the syringe to a point at which one volume unit is directed into the syringe.

Still other features of the present assembly include the provision of the retaining means which allows the securement of the bottle of medicine into the opposite open end of the base which is also defined by a surrounding collar. This will prevent inadvertent removal or displacement of the bottle of medicine from the base and insures that the needle of the syringe is properly placed on the interior of the bottle. A pulling force exerted on the bottle will serve to efficiently remove the bottle from the corresponding open end of the base and from the retaining means which removably secures it in its operative position.

In operation, the elongated shaft, being externally threaded, is rotated to its fullest inward position such that the free end thereof is closest to the corresponding end of the plunger of the syringe. The operator then, knowing the amount of dosage required to be dispensed into the barrel of the syringe then rotates the shaft in an opposite direction causing it to withdraw a certain distance from the interior of the base. The operator, being sightless or sight impaired, determines the proper distance of withdrawal of the threaded shaft by listening to the number of "clicking sounds" generated by the indicator means associated with the threaded shaft. As set forth above the distance between each of the threads on the externally threaded elongated shaft is such that one click is equivalent to the distance the plunger of the syringe need be withdrawn to allow passage into the barrels of the syringe a given unit volume such as one cubic centimeter. For example, if ten cubic centimeters are desired to be withdrawn into the barrel of the syringe for subsequent injection into the body, the operator will rotate the elongated shaft until he hears ten "clicks." In this position the free end of the shaft is spaced from the free end of the plunger. The plunger is then extracted from the barrel of the syringe up to a point where it is in abutting engagement with the inner free end of the shaft. This will of course cause a negative pressure within the barrel of the syringe and cause the medicine in the medicine bottle to be passed into the syringe. The syringe is then removed from the base and the bottle of medicine and it now contains the proper amount of medicine in the barrel of the syringe.

DESCRIPTION OF THE DRAWINGS

For a fuller understanding of the nature of the present invention, referenced is had to the following detailed description taken in connection with the accompanying drawings in which:

FIG. 1 is a perspective view showing the syringe filling assembly of the present invention with a syringe and medicine bottle mounted thereon.

FIG. 2 is a sectional view along line 2—2 of FIG. 1.

FIG. 3 is a sectional view along line 3—3 of FIG. 1.

FIG. 4 is a schematic representation showing placement of various components as well as the syringe and medicine bottle.

FIG. 5 is a perspective view in partial phantom showing operation and handling of the subject assembly.

FIG. 6 is a top view of the embodiment of FIG. 1 absent the syringe and medicine bottle.

DETAILED DESCRIPTION OF PREFERRED EMBODIMENT

As shown in the accompanying drawings, the present invention is directed to a syringe filling assembly specifically designed to meter out proper doses of liquid medicine and which is generally indicated as ten in FIG. 1. The assembly includes an elongated base 12 having an open side 14 extending along a majority of the length thereof. The open side 14 provides external access to an interior surface as at 16. The interior surface 16 has a plurality of recesses as at 18, 19, 20, etc., Which are specifically mentioned and configured to removably receive a conventional syringe 22 as well as a bottle of liquid medicine 24. In the operative position shown in FIGS. 1 and 5 the syringe 22 includes a needle 25 which is penetrated into the interior of the medicine bottle 24 so as to come in contact with and remove liquid medicine contained therein.

The base further includes two oppositely disposed open ends defined by surrounding collars 26 and 28. The first open end and collar 26 is designed to surround and movably and matingly engage an elongated shaft generally indicated as 30. The elongated shaft has an outer most end defined by a knob as at 32 and an inner most end defined by a stop member 34. The external surface of the shaft 30 is threaded along its length. An important part of the present invention is that each of the threads as at 36 are dimensioned and configured and more specifically spaced apart a specific distance to accommodate a specific amount of volume of fluid passing between the container 24 and barrel of the syringe 22. The inner surface of the collar 26 is internally threaded so as to threadedly engage the exterior surface of the shaft 30. By virtue of this movable inner connection, rotation of the knob 32 in opposite directions will cause the shaft to travel towards or away from the syringe 22 as desired.

The present invention further includes an indicator means generally indicated as 40. The indicator means 40 is attached to the collar 26 in a manner which allows it to pass through the collar and into contact with the various threads 36 of the elongated shaft 30. One preferred embodiment of the indicator means 40 would be a ball bearing 41 mounted on the end of a biasing spring 45 such that the ball bearing 41 is forced into movable engagement with each of the threads 36 by virtue of the force exerted thereon by the spring 43. As the threads pass by the ball bearing, they will cause it to move against the biasing force of spring 43 to contact the next successive thread. When the ball falls from one thread to the next an audible "clicking sound" will be generated. This will indicate to the sightless operator that the elongated shaft 30 has been withdrawn a distance of one thread. The threads are specifically structured, dimensioned and configured to be spaced apart a sufficient distance to be equivalent to the passage into the barrel of the syringe 22 one unit volume of liquid such as one cubic centimeter.

This will be explained in greater detail hereinafter when referring to the operation of the subject assembly.

Another feature of the present invention is the existence of a retainer member 42 which may also be a biasing spring 42' disposed to removably engage an exterior surface of the medicine container 24. The medicine container is passed to the interior of the collar 28 and is held in its operative position within a recess portion 18 of the base by virtue of the biasing spring 42' of retaining means 42 coming into engagement with the outer surface of the Container 24. When such engagement occurs, the biasing spring 42' will be forced at least partially outward from the interior of collar 28 as shown in FIG. 3 by directional arrow 47'. However, the medicine container 24 is only removably retained within the collar 28 and open end 28' such that it can be removed from its operative position upon a pulling force being exerted from its exteriorly located end.

In operation, the shaft 30 is rotated to its inner most position indicated by the position line in FIG. 4 as 44. Once it is positioned and once the sightless operator knows the amount of dosage to be passed into the barrel of the syringe 22, the knob 32 is rotated so as to retract the elongated shaft 30 from the interior of the base say a distance of ten audible clicks. This distance is indicated as 45 in FIG. 4. The inner end or stop member 34 of the shaft 30 is thereby positioned in accordance with the position 46 of FIG. 4. Once so positioned the plunger as at 47 is withdrawn from the interior of the barrel of the syringe 22 till it abuts the stop member 34 as shown in FIG. 4. The distance 45 thereby represents the distance the plunger will have to be withdrawn to remove the proper dosage from the interior of the container 24. It should be again noted that the operator knows that the stop member 34 is properly placed because he has heard for example ten clicks generated by the indicator means 40 as described above. Positions of the aforementioned ball bearing 41 as at 50 and 51 are schematically represented by two clicks and/or two threads being engaged by the ball bearing 41 as it passes along and comes in contact with the indicator means 40.

The syringe 22 is then removed from the base and container 24 and is ready for injection into the patient.

Now that the invention has been described,

What is claimed is:

1. A syringe filling assembly designed to allow metering of a liquid into a syringe by a sightless person, said assembly comprising:
   a) an elongate base having an open side extending along a majority of the length thereof and said base terminating in opposite ends,
   b) said base including an interior surface extending along the length of said base and exposed in accessible communication with said open side,
   c) said inner surface of said base comprising a plurality of recesses integrally formed therein and configured to receive an outer surface portion of the syringe and medicine container therein,
   d) metering means movably mounted on said base and structured and disposed for regulating a quantity of liquid passing into the syringe from the medicine container,
   e) said metering means structured and disposed to be selectively movable between an inwardly extended position and an outwardly protracted position relative to both said base and the syringe when mounted on said base,
   f) said metering means comprising an elongated shaft movably connected to a first of said opposite ends o said base and movable through said first end towards and away from the syringe,
   g) said first end including an open construction defined by a first collar configured in surrounding relation to at least a portion of said metering means,
   h) said first collar comprising an internally threaded construction integrally formed along said interior surface thereof; said elongated shaft comprising an externally threaded construction disposed in movable, mating, threaded engagement with said interior surface of said first collar, i) an indicator means structured and disposed to engage a plurality of threads of said externally threaded construction, said indicator means structured and disposed to produce a plurality of successive sounds upon engagement with a plurality of successive threads of said externally threaded construction of said elongated shaft, and j) said indicator means and said threaded construction of said elongated shaft being cooperatively calibrated relative to one another so as to indicate one unit volume of medicine being dispensed per one of the plurality of successive sounds being produced by said indicator means.

2. An assembly as in Claim 1 wherein said opposite ends of said base comprise a second end oppositely disposed to said first end and adapted to removably support the medicine container therein.

3. An assembly as in Claim 2 wherein said second end has an open construction structure and disposed to allow passage of the medicine container therein and into engagement with the syringe.

4. An assembly as in claim 3 wherein said open construction of said second end is defined by a second collar configured and dimensioned for surrounding engagement with the medicine container.

5. An assembly as in claim 4 further comprising retaining means mounted on said second collar and disposable into engaging relation with the medicine container and adapted for removably retaining the medicine container within said second collar.

* * * * *